United States Patent [19]

Vickers et al.

[11] 4,338,476
[45] Jul. 6, 1982

[54] ALKYLAROMATIC HYDROCARBON DEHYDROGENATION PROCESS

[75] Inventors: Anthony G. Vickers, Arlington Heights; Robert F. Zabransky, Oak Brook, both of Ill.

[73] Assignee: UOP Inc., Des Plaines, Ill.

[21] Appl. No.: 969,619

[22] Filed: Dec. 14, 1978

Related U.S. Application Data

[63] Continuation-in-part of Ser. No. 810,322, Jun. 27, 1977, abandoned.

[51] Int. Cl.³ .............................................. C07C 5/333
[52] U.S. Cl. .................................... 585/440; 585/441; 585/442; 585/443
[58] Field of Search ................ 585/440, 441, 442, 443

[56] References Cited

U.S. PATENT DOCUMENTS

| 3,256,355 | 6/1966 | Gelman et al. | 260/669 R |
|---|---|---|---|
| 3,409,689 | 11/1968 | Ward | 260/669 R |
| 3,515,765 | 5/1968 | Berger | 260/669 R |
| 3,515,766 | 5/1968 | Root et al. | 260/669 R |
| 3,515,767 | 6/1970 | Carson et al. | 260/669 R |
| 3,527,699 | 9/1970 | King | 260/669 A |
| 3,690,839 | 10/1970 | Jones | 260/669 R |
| 3,702,346 | 11/1972 | Kellar | 260/669 R |
| 3,751,232 | 8/1973 | Borre et al. | 260/669 R |
| 3,847,968 | 11/1974 | Hughes | 260/669 R |

Primary Examiner—Delbert E. Gantz
Assistant Examiner—Joseph A. Boska
Attorney, Agent, or Firm—James R. Hoatson, Jr.; John F. Spears, Jr.; William H. Page, II

[57] ABSTRACT

Alkylaromatic hydrocarbons are dehydrogenated in admixture with steam, with the dehydrogenation zone effluent being condensed to form a water stream which is purified in a stripping column. The stripping column is reboiled by indirect heat exchange against the effluent of the dehydrogenation zone. The steam-rich overhead vapor stream of the stripping column is mixed directly into the dehydrogenation zone feed stream without intermediate condensation or pressurization.

1 Claim, 1 Drawing Figure

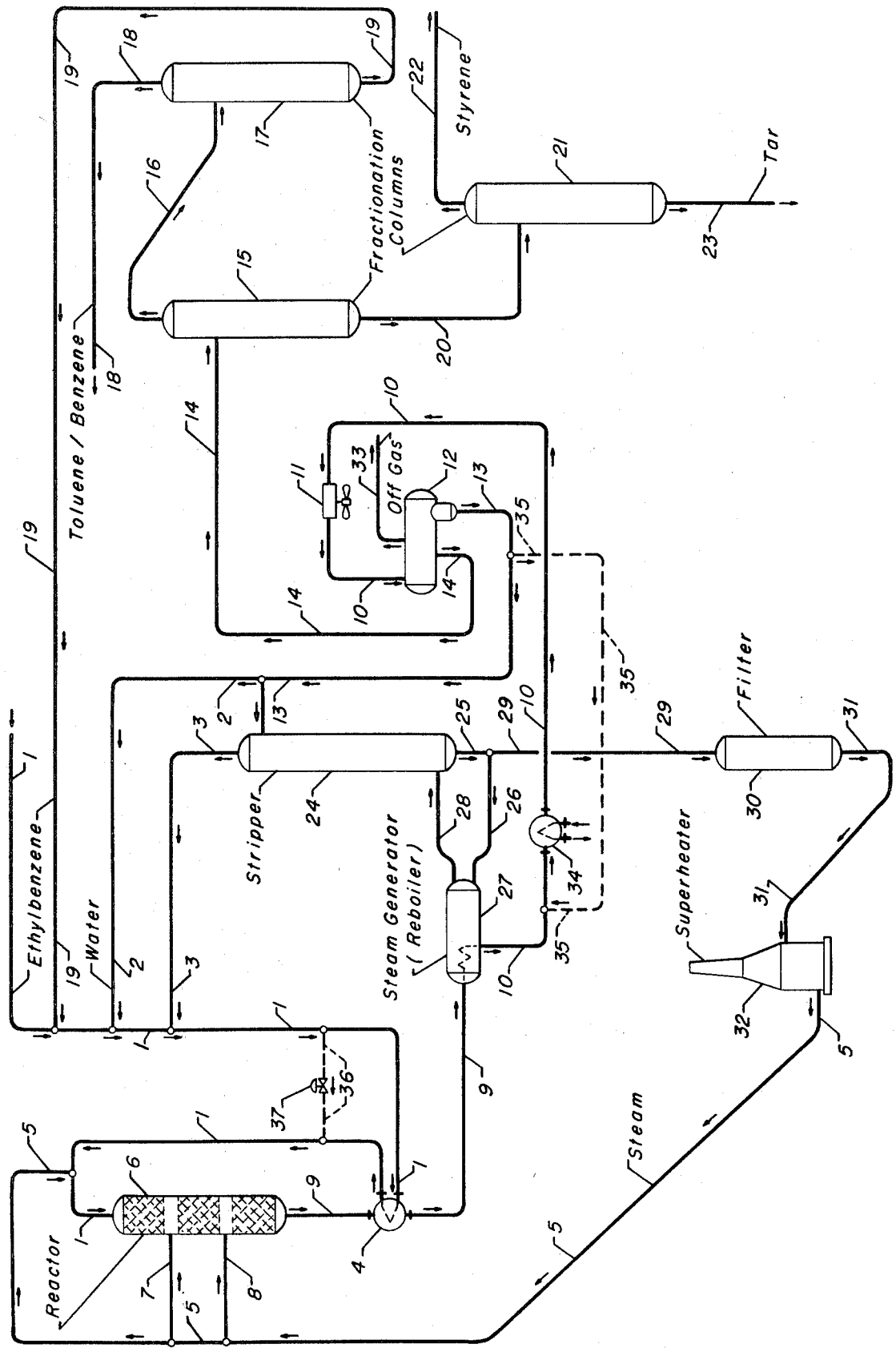

ALKYLAROMATIC HYDROCARBON DEHYDROGENATION PROCESS

CROSS-REFERENCE TO RELATED APPLICATION

This application is a continuation-in-part of our prior copending application Ser. No. 810,322 filed on June 27, 1977 and now abandoned. The teachings of our prior application are incorporated herein by reference.

FIELD OF THE INVENTION

The invention relates to the processing of mineral oils. The invention also relates to a process for the deydrogenation of alkylaromatic hydrocarbons. It more specifically relates to a process for the dehydrogenation of ethylbenzene wherein water is condensed from the dehydrogenation zone effluent and then purified and recycled as steam used within the dehydrogenation zone. The invention therefore relates to processes similar in nature to those found, for example, in Classes 260-669 and 203-2.

PRIOR ART

The dehydrogenation of aromatic hydrocarbons is well described in the prior art. It is performed commercially for the production of styrene from ethylbenzene to fulfill the sizable demand for this polymer precursor. The product styrene may then be polymized with itself or it may be copolymerized with butadiene, isoprene, acrylonitrile, etc. Processes for the dehydrogenation of alkylaromatic hydrocarbons are often integrated with an alkylation process for the production of the alkylaromatic hydrocarbon as shown in U.S. Pat. No. 3,525,776 (Cl. 260-699).

The vapor phase dehydrogenation of ethylbenzene in admixture with superheated steam is widely described in the art as shown by U.S. Pat. Nos. 3,118,006 (Cl. 260-669); 3,402,212; 3,515,763 and 3,847,968 issued to R. E. Hughes. The steam is used as a diluent to reduce the partial pressure of the styrene and to supply sensible heat consumed by the endothermic dehydrogenation reaction. Toluene or other substances may also be circulated through the reaction zone as shown in U.S. Pat. No. 3,409,689. It is a customary practice to recover heat from the dehydrogenation zone effluent stream by indirect heat exchange against the feed stream or other streams and by the generation of steam. This is described in more detail in U.S. Pat. No. 3,473,519 (Cl. 122-32). The water and $C_6$-plus hydrocarbons in the dehydrogenation zone effluent stream are then condensed to allow the facile phase separation of the water and hydrocarbons by decantation. This is described in U.S. Pat. No. 3,702,346 issued to J. S. Keller and in British Patent No. 1,238,602.

The styrene is then recovered from a resultant hydrocarbon liquid fraction by fractionation. The fractionation of styrene may be performed in the multi-column system shown in previously cited U.S. Pat. No. 3,525,776 or in other systems known in the art. The separation of the styrene in a single fractionation column is described in U.S. Pat. Nos. 3,408,263; 3,408,264 (Cl. 203-2) and 3,408,266 (Cl. 203-9).

The aqueous fraction formed by the condensation of the dehydrogenation zone effluent stream is withdrawn from the product settler as a water stream. It is known in the art to recycle at least a portion of this stream to the dehydrogenation zone as the superheated steam fed to this zone. It is also known that it is beneficial to remove styrene and certain other hydrocarbonaceous materials from this water stream before it is passed into the superheater. This purification of the condensate is performed to lessen or prevent the formation of coke deposits within the heater tubes used in the superheater.

The purification of the water stream is customarily accomplished by stripping the more volatile hydrocarbons from the condensate. This is shown in U.S. Pat. Nos. 3,515,765 (Cl. 260-669) issued to C. V. Berger and 3,527,699 (Cl. 210-21) issued to N. B. King. In these references, the overhead vapor stream of the water stripping column is directed into the reaction zone effluent phase separation zone and the steam in this stream is therefore condensed. The latter reference discloses the total recycle of the hydrocarbon content of the resultant aqueous condensate. However, it fails to suggest the recycling and reuse of the steam present in the overhead vapor stream of the water stripping column in the manner described herein.

U.S. Pat. No. 3,515,766 issued to W. N. Root describes the preferred utilization of a filter to further purify the bottoms stream of the water stripping column. In this reference, the overhead vapor stream of the stripping column is admixed with the cooled dehydrogenation zone effluent stream. As is customary in the art, a portion of the purified bottoms stream is superheated for use in the dehydrogenation zone. In U.S. Pat. No. 3,515,767 issued to D. B. Carson, the stripping column overhead vapor stream is also admixed with the dehydrogenation zone effluent stream. However, the stripping column bottoms stream is heat exchanged against the dehydrogenation zone effluent stream to form low pressure steam. This steam is then compressed, with a portion being used to reboil the product fractionators.

The dehydrogenation of ethylbenzene is an energy intensive process and a great many other systems have been developed to increase the energy efficiency of the process. For instance, in U.S. Pat. No. 3,256,355, the dehydrogenation zone effluent stream is first cooled by heat exchange against the feed stream and then used to generate low pressure steam. This steam is then compressed for use in reboiling the product fractionators. In another embodiment of this reference, the cooled and scrubbed dehydrogenation zone effluent stream is itself compressed and used to reboil the product fractionators.

The subject process is distinguished from the prior art in several ways. For instance, it is believed that heretofore the overhead vapor stream of the condensate stripping column has not been passed directly into the reaction zone. Instead, it has been condensed in an overhead vapor condenser or by admixture with the effluent of the dehydrogenation zone and subsequent cooling. It is also believed that the prior art does not suggest the recovery of low-level heat from the dehydrogenation zone effluent stream by reboiling the condensate stripping column by indirect heat exchange against the cooled dehydrogenation zone effluent stream. Further, the prior art does not teach the manner in which the steam generated by this indirect heat exchange may be used twice in a dehydrogenation process. In comparison, in the subject process this steam is first used to reboil the stripping column and is then used in the reaction zone as a diluent and heat source.

BRIEF SUMMARY OF THE INVENTION

The invention provides a process for the vapor phase dehydrogenation of alkylaromatic hydrocarbons wherein the aqueous condensate formed by cooling the reaction zone effluent stream is purified in a stripping column. This stripping column is reboiled with steam produced by the indirect heat exchange of the cooled reaction zone effluent stream against the bottoms liquid of the stripping column immediately prior to the condensation of the effluent stream. The resultant steam rises through the stripping column and forms part of the overhead vapor stream. The stripping column is operated within a relatively narrow pressure range which allows the column to be reboiled in this manner and which also allows the stripper overhead vapor stream to be passed directly into the reaction zone without being compressed. The stripping column overhead vapor is not condensed but is admixed directly into the reaction zone feed stream.

The subject process therefore reuses the steam generated to reboil the water stripping column which emerges as part of the stripper overhead vapor stream. This internal recycling of the steam avoids energy losses necessarily associated with condensing the overhead vapor stream. The reuse of the steam also lowers the amount of fresh steam which must be generated to provide any desired steam to hydrocarbon ratio in the dehydrogenation zone. The invention therefore provides a significant reduction in both the capital and utilities cost of a dehydrogenation process.

BRIEF DESCRIPTION OF THE DRAWING

Applicant's drawing is a schematic view of the process flow of this invention.

DESCRIPTION OF THE DRAWING

The Drawing illustrates the invention as it may be employed for the production of styrene by the dehydrogenation of ethylbenzene. For clarity and simplicity, various subsystems and apparatus normally required for the successful operation of the process have not been shown. These items include flow and pressure control valves, control and monitoring systems, reactor and fractionator internals, etc., which may be of customary design. This representation of the preferred embodiment is not intended to preclude from the scope of the invention those other embodiments set out herein or which are the result of reasonable and normal modification of these embodiments.

Referring now to the Drawing, a feed stream of relatively pure liquid ethylbenzene enters the process through line 1. To the feed stream are added a recycle ethylbenzene stream from line 19, an optional liquid water stream from line 2 and a stream of stripping column overhead vapors from line 3. The feed stream continues through line 1 and may be heated by a means not shown, such as by heat exchange against steam or fractionator effluent streams. The feed stream is heat exchanged and preferably at least partially vaporized in heat exchanger 4 and is then commingled with superheated steam from line 5. A portion of the feed stream may be diverted through line 36 at a rate controlled by valve 37 to regulate the amount of heat transferred in the feed-effluent exchanger 4. It is then passed into a dehydrogenation zone contained within reactor 6. The effluents of the first and the second beds of catalyst are admixed with streams of superheated steam from lines 7 and 8 respectively. This counter-acts the endothermic dehydrogenation reaction and raises the temperature of the reactants above the minimum temperature of the applicable dehydrogenation conditions.

A vaporous dehydrogenation zone effluent stream is removed from the dehydrogenation zone in line 9 and is cooled in heat exchanger 4 by indirect heat exchange against the feed stream. The effluent stream may be further cooled in additional heat exchangers not shown. It is then passed into a steam generation zone is vessel 27 which functions as the reboiler of the water stripping column 24. It is therein indirectly heat exchanged to generate steam passed into the stripping column. The dehydrogenation zone effluent stream is then passed through a heat exchanger 34 and a cooler 11 via line 10. It is thereby cooled to a temperature which effects the condensation of the majority of the $C_6$-plus hydrocarbons and water contained in this stream, and it is then injected into a phase separation zone 12 commonly referred to as the product settler. Uncondensed gases including hydrogen, methane, water vapor and some heavier hydrocarbons are removed from the product settler in line 33. Some of these heavier hydrocarbons are condensed and returned to the product settler by a customary means not shown.

The condensed portion of the dehydrogenation zone effluent stream is allowed to separate into a hydrocarbon fraction and an aqueous fraction which contains an equilibrium concentration of the various hydrocarbons present in the product settler. The hydrocarbon fraction is withdrawn as a liquid hydrocarbon stream in line 14 and passed into a fractionation zone comprising fractionation columns 15, 17 and 21. The overhead stream of column 15 is removed in line 16 and contains the benzene and toluene which is produced in the process, and which may be recirculated. It also contains ethylbenzene which was not dehydrogenated in the reactor. This overhead stream is separated in column 17 into the ethylbenzene stream recycled in line 19 and an overhead stream of benzene and toluene shown being removed in line 18. The bottoms stream of column 20 comprises styrene and any high boiling impurities and is passed into column 21 through line 20. In this column, the styrene is recovered as an overhead stream removed in line 22, while the high boiling materials, commonly referred to as tar, are removed through line 23. Other fractionation systems known to the art may also be used to recover the styrene.

The aqueous fraction formed by the phase separation of the condensed dehydrogenation zone effluent is withdrawn from the product settler as a water stream carried by line 13. Although not preferred, a portion of the water stream may be passed through line 35 and injected into the dehydrogenation zone effluent. Preferably, a first portion of the water stream is passed through line 2 and admixed with the feed stream. A remaining second portion of the water stream is passed into the top of a stripping column 24. This column is operated under conditions which effect the removal of substantially all of the easily distillable $C_6$ and $C_8$ hydrocarbons which are dissolved in the entering water. These hydrocarbons include benzene, styrene and ethylbenzene and are removed from the stripping column as part of the overhead vapor stream carried by line 3.

A total bottoms stream comprising water which is substantially free of $C_6$ and $C_8$ hydrocarbons is removed in line 25. A first portion of this total bottoms stream is passed through line 26 into the steam generation zone or reboiler 27. It is therein vaporized to form the steam transferred by line 28 to the bottom of the stripping column. This steam is formed at a rate sufficient to reboil the water stripping column. This produces an overhead vapor stream which is rich in steam and which is mixed directly into the feed stream.

A net bottoms stream is withdrawn in line 29. This net bottoms is preferably passed through a filter 30 which removes high boiling hydrocarbons which are not removed by the stripping process. The purified net bottoms stream emerges in line 31 and is vaporized and the superheated in superheater 32 to form the superheated steam carried by line 5. The superheated steam may alternatively be formed from a completely different water source, and the purified net bottoms stream may be utilized in a different manner.

DETAILED DESCRIPTION

The dehydrogenation of various alkylaromatics, such as diethylbenzene, ethyltoluene, propylbenzene and isopropylbenzene may be performed in the subject process. However, since commercial emphasis is placed on the use of ethylbenzene as the feedstock, the subject invention will be described as it would be used in a process for the dehydrogenation of ethylbenzene to produce styrene.

The dehydrogenation process is endothermic, and therefore most dehydrogenation processes admix superheated steam with the ethylbenzene before it is fed into the reaction zone. The superheated steam acts as a heat source which allows a greater amount of dehydrogenation to be performed in a catalyst bed before the temperature of the ethylbenzene becomes too low for the reaction to proceed appreciably. The effluent of the dehydrogenation zone is normally condensed to effect the sepration of the hydrocarbons from the water. It is desirable to reuse the water which is separated in this manner by recycling the water to a steam generation zone. This may be any boiler or waste heat steam generator, but is preferably a zone in which the superheated steam used within the dehydrogenation zone is formed. This recycling is desirable because it reduces the amount of makeup water which must be pretreated and also because it eliminates the problem of disposing of hydrocarbon-containing water.

The water which is removed from the phase separation zone will have dissolved in it a near equilibrium concentration of the various hydrocarbons which are present in hydrocarbon liquid phase also present in this zone. It will therefore contain a mixture of various aromatic hydrocarbons, such as ethylbenzene, styrene, benzene and toluene and various polymeric compounds normally referred to as tar. It has been recognized in the art that the styrene, ethylbenzene and tar should be removed before this water is reused in steam generation. If this is not done, these hydrocarbons may cause a severe coking problem within the heat exchange tubes of a high temperature heater such as the steam superheater. This in turn may cause a premature shut-down of the process. Furthermore, under certain conditions, the styrene often tends to form polymeric coatings on the surface of heat exchanger tubes. This reduces the heat transfer efficiency of the exchanger and may eventually plug the tubes.

The prior art therefore purifies the recycled water by the sequential steps of stripping and filtration. The stripping step is performed under conditions which remove the relatively volatile hydrocarbons such as $C_6$ and $C_8$ aromatics. The filtration removes the high-boiling tar which is not removed in the stripping step and often comprises the passage of the net stripper bottoms through a bed of activated charcoal. The stripping of the condensate water consumes a fair amount of energy and therefore increases the utility costs of the dehydrogenation process. However, the alternative of disposing of the condensate water imposes the costs of meeting environmental standards.

It is an objective of this invention to provide a process for the dehydrogenation of alkylaromatic hydrocarbons. It is another objective of this invention to provide a process for the vapor-phase dehydrogenation of ethylbenzene while commingled with steam, in which process the steam is condensed and the resultant condensate is stripped of volatile hydrocarbons. It is yet another objective to lower the utilities and capital costs of a process for the dehydrogenation of ethylbenzene.

In the subject process, these objectives are met by utilizing the sensible heat available within the effluent of the dehydrogenation zone effluent to reboil the water stripping column while it is maintained at a superatmospheric pressure. This effects the stripping of the condensate water. It also has the advantage of eliminating a costly compressor, since the column is operated at a pressure above that of the feed stream to the dehydrogenation zone and the overhead vapor admixes with the feed stream without compression. Unless otherwise specified, all column pressures recited herein refer to the pressure at the top of the column. The capital cost of the process is also held down by the absence of an overhead condenser on the water stripping column.

A second advantage of this method of operating is that the latent heat of vaporization contained within the stripper overhead stream is recovered when it is admixed with the feed stream. This more efficient than attempting to recover this heat by indirect heat exchange and hence improves the utility economics of the process. That is, in the subject process, there is no heat lost by cooling and condensing the stripping column overhead vapor stream as in the prior art. Instead, the steam generated to reboil the stripping column is used twice. It is first used to reboil the stripping column and is then used as part of the feed stream. The subject process is therefore an improvement over prior art processes wherein the stripper overhead stream is admixed with the effluent of the dehydrogenation zone and then condensed.

The efficient recovery of heat from the stripping column overhead vapor stream is made difficult by relatively low temperature of this stream. No suitable process stream may be available for heat exchange against the overhead vapor stream for the purpose of recovering the available "low level" heat. Therefore in the past a large amount of this heat was often rejected by cooling the overhead vapor by heat exchange against cooling water or ambient air. The subject process recovers and uses all of the heat in the overhead vapor stream.

The invention is further illustrated by this example of a process utilizing the subject water stripping and vapor recirculation method. About 800 mph (moles per hour) of fresh ethylbenzene enter in a feed stream at 300° F. and 25 psig. It is admixed with a 550 mph stream of recycled ethylbenzene and about 3,840 mph of water. It is also admixed with the water stripper overhead stream and with about 1030 mph of steam having a temperature of 270° F. The resultant combined feed stream is a two phase stream having a temperature of about 251° F. It exits the feed-effluent heat exchanger at a pressure of about 15 psig. and a temperature of about 996° F. The combined feed stream is then fed into the dehydrogenation zone in admixture with superheated steam having a temperature of about 1470° F.

The effluent of the dehydrogenation zone has a temperature of about 1145° F., a pressure of about 5 psig. and a flow rate of approximately 24,800 mph. It is cooled to about 498° F. in the feed-effluent heat exchanger and fed into the reboiler of the water stripping column at a pressure of about 3.5 psig. The dehydrogenation zone effluent exits the reboiler at a temperature of about 306° F. It is then cooled to about 150° F. to condense most of the water and heavier hydrocarbons and passed into a phase separation zone maintained at approximately atmospheric pressure.

The phase separation zone, or product settler, is maintained at quiescent conditions which promote the separation of the hydrocarbon and aqueous liquid phases and the release of bubbles from the liquid. The uncondensed hydrogen, water vapor, carbon dioxide, methane and other light gases are removed at the rate of 2,000 mph. This vapor stream has an average molecular weight of about 17.3 and is passed into a recovery system wherein it is compressed to 25 psig. and cooled to about 100° F. This causes the condensation of about 40 mph of hydrocarbons having an average molecular weight of approximately 102 and about 19 mph of water, both of which are returned to the product settler. The hydrocarbon stream withdrawn from the phase separation zone has a flow rate of about 1,340 mph, and the water stream has a flow rate of about 23,250 mph. The design and operation of the phase separation zone is well understood by those skilled in the art. It may alternatively be operated at a subatmospheric pressure, as from about 200 to 600 mg Hg absolute, as is taught in U.S. Pat. No. 3,702,346.

About 1,095 mph of the water stream from the phase separation zone is admixed with the dehydrogenation zone effluent as a quench liquid. The remaining water is divided between a first portion, which is that added to the feed stream, and a second portion which is passed into the top of the water stripper. This column is reboiled through the use of an external reboiler in which the vapor phase dehydrogenation zone effluent is indirectly heat exchanged against water removed from the bottom of the stripping column. This produces about 1,915 mph of steam which is fed into the stripping column at a pressure of approximately 27 psig. and a temperature of about 270° F. The stripping column overhead stream has a flow rate of about 555 mph and a temperature of approximately 267° F. The net bottoms stream has a flow rate of about 19,680 mph. A column having an internal diameter of about 6½ feet and containing 20 decks is adequate for this step of the process. The net bottoms stream is passed through a charcoal filter.

The product styrene may be recovered from the hydrocarbon stream by using any one of several fractionation systems known in the art. This fractionation will preferably yield a relatively pure stream of ethylbenzene, which is recycled, and a benzene/toluene stream of about 70 mph. These two aromatic hydrocarbons are by-products of the dehydrogenation reaction. They may be recycled in part as taught in U.S. Pat. No. 3,409,689 and British Patent No. 1,238,602 or entirely rejected from the process. Styrene is recovered at the rate of about 706 mph. If desired, methods other than fractionation may be used to recover the styrene. For instance, U.S. Pat. No. 3,784,620 teaches the separation of styrene and ethylbenzene through the use of a polyamide permeation membrane such as nylon-6 and nylon 6,10. U.S. Pat. No. 3,513,213 teaches a separatory method employing liquid-liquid extraction in which anhydrous silver fluoroborate is used as the solvent. Similar separatory methods utilizing cuprous fluoroborates and cuprous fluorophosphates are described in U.S. Pat. Nos. 3,517,079; 3,517,080

The effluent of an ethylbenzene dehydrogenation process may be separated in a fractionation zone such as shown in the Drawing or in the manner described in U.S. Pat. No. 3,525,776. In this reference, the hydrocarbonaceous phase removed from the phase separation zone is passed into a first column referred to as a benzene-toluene column. This column is operated at a subatmospheric pressure to allow its operation at lower temperatures and hence reduce the rate of styrene polymerization. Various inhibitors such as elemental sulfur, 2,4-dinitrophenol or a mixture of N-nitroso diphenyl amine and a dinitroso-o-cresol are injected into the column for this same purpose. Preferably, sulfur is also introduced into this column by returning at least a portion of the high molecular weight material separated from the bottoms stream of a styrene purification column. A more detailed description of this is contained in U.S. Pat. Nos. 3,476,656; 3,408,263; and 3,398,063. There is effected within the benzene-toluene column a separation of benzene and toluene from the effluent to produce an overhead stream which is substantially free of styrene and ethylbenzene. This stream preferably contains at least 95 mol.% benzene and toluene. The bottoms of the benzene-toluene column is passed into a second fractionation column from which ethylbenzene is removed as an overhead product and recycled. The bottoms stream of this column is then purified to obtain the styrene. Those skilled in the art are competent in the design and operation of the required fractionation systems.

In accordance with this description, the invention may be characterized as a process for dehydrogenating an alkylaromatic hydrocarbon which comprises the steps of admixing a hereinafter specified vapor stream which comprises steam and the alkylaromatic hydrocarbon into a feed stream comprising an alkylaromatic hydrocarbon; passing the feed stream as a vapor into a catalytic dehydrogenation zone maintained at dehydrogenation conditions; removing from the dehydrogenation zone a vaporous effluent stream comprising the alkylaromatic hydrocarbon, an alkenylaromatic hydrocarbon and steam; cooling the effluent stream by indirect heat exchange against the feed stream; further cooling the effluent stream and simultaneously reboiling a water stripping column by generating steam by the indirect heat exchange of the effluent stream against water removed from the bottom of the water stripping column; further cooling the effluent stream and condensing substantially all of the steam in the effluent stream, and passing the effluent stream into a phase separation zone operated at conditions effective to produce a liquid hydrocarbon fraction comprising the alkenylaromatic hydrocarbon and an aqueous fraction containing dissolved $C_8$ hydrocarbons; withdrawing the liquid hydrocarbon fraction from the phase separation zone as a hydrocarbon stream, and recovering the alkenylaromatic hydrocarbon from the hydrocarbon stream; withdrawing the aqueous fraction from the phase separation zone as a water stream; feeding at least a first portion of the water stream into an upper portion of the water stripping column under conditions effective to form a stripping column overhead vapor stream comprising steam and substantially all of the $C_8$ hydrocarbons dissolved in the first portion of the liquid water stream, said conditions including a superatmospheric pressure greater than that maintained in the dehydrogenation zone but sufficiently low to allow the stripping column to be reboiled by indirect heat exchange against the effluent stream after the effluent stream has been cooled by heat exchange against the feed stream; admixing the stripper overhead vapor stream directly into the feed stream as the aforementioned vapor stream without intermediate cooling or compression; and removing a net bottoms stream comprising water which is substantially free of $C_8$ hydrocarbons from the water stripping column.

The present invention may be applied to any process for the dehydrogenation of alkylaromatic hydrocarbons wherein the dehydrogenation zone effluent is condensed to form a liquid water phase and a portion of this water is to be recycled for the production of steam. The specific mode of operation of the reaction zone or the composition of the catalytic material is not determinative of the usefulness of the invention. The examples and description herein which refer specifically to the dehydrogenation of ethylbenzene are therefore not intended to so limit the invention. This process may be applied to the dehyrogenation of other alkylaromatic hydrocarbons such as those previously listed and also to alkylaromatic hydrocarbons having other ring structures, including naphthalenes and anthracene compounds.

The dehydrogenation zone preferably comprises two or three beds of dehydrogenation catalyst with means for the intermediate addition and admixture of steam. Suitable systems for this are presented in U.S. Pat. Nos. 3,498,755; 3,515,763; and 3,751,232. The catalyst eds may be contained in separate reaction vessels and may have either a cylindrical or an annular shape. Different catalysts may be used in different beds as described in U.S. Pat. No. 3,223,743. Such catalysts generally consist of one or more metallic components selected from Groups VI and VIII of the periodic table. These metallic components are typically carried on a refractory inorganic oxide material such as alumina, silica, boria or mixtures thereof. One typical catalyst comprises 85% by weight ferric oxide, 2% chromia, 12% potassium hydroxide and 1% sodium hydroxide. A second typical catalyst comprises 90% by weight iron oxide, 4% chromia and 6% potassium carbonate. Methods for preparing suitable catalysts are well known in the art. This is demonstrated by the teachings of U.S. Pat. No. 3,387,053, which describes the manufacture of a catalytic composite of at least 35 wt.% iron oxide as an active catalytic agent, from about 1 to 8 wt.% zinc or copper oxide, about 0.5 to 50 wt.% of an alkali promoter, and from about 1 to 5 wt.% chromic oxide as a stabilizer and a binding agent. Catalysts preferably employed are available commercially and commonly referred to as "Shell 105", "Shell 205" and "CCI 97".

Dehydrogenation conditions in general include a temperature of about 1000° F. to about 1800° F. and preferably about 1050° F. to about 1250° F. The temperature required for any specific unit will depend on the activity of the catalyst employed. The pressure maintained within the dehydrogenation zone is generally quite low and may range from subatmospheric to 100 psig., with a preferred pressure range of inlet pressures being from about 2.0 to 10 psig. The combined feed stream is charged to the dehydrogenation zone at a liquid hourly space velocity, based on liquid hydrocarbon charge at 60° F., of about 0.1 hr.$^{-1}$ to about 1.0 hr.$^{-1}$, and preferably from 0.2 to 0.7 hr.$^{-1}$.

As previously mentioned, the alkylaromatic to be dehydrogenated is admixed with superheated steam to counteract the temperature lowering effect of the dehydrogenation reaction. Preferably, the steam is admixed with the feed stream and also added at intermediate points within the reaction zone. Some processes utilize indirect heat exchange of the reactants or heating elements within the catalyst bed instead of this intermediate steam addition. The steam and the alkylaromatic hydrocarbon can be separately heated and commingled prior to contacting the reactants with the catalyst, or the steam and alkylaromatic can be first commingled and then heated. When ethylbenzene is being dehydrogenated, the space velocity, the rate of steam admixture and the inlet temperature are adjusted to result in the effluent of each catalyst bed having a temperature of about 1100° F. Preferably, steam is admixed with the feed stream to the dehydrogenation zone at a rate of about 0.65 to about 1.0 pounds of steam per pound of ethylbenzene. A second portion is added to the effluent of the first catalyst bed at a rate of about 1.0 to about 1.2 pounds of steam per pound of effluent and a third portion is added to the effluent of the second bed at a rate of about 0.8 to about 1.3 pounds per pound of effluent. These rates are normally adjusted such that the total effluent stream from the dehydrogenation zone will contain from about 3 to about 6 pounds of steam per pound of styrene. Lower steam to hydrocarbon ratios may, however, be used.

The effluent stream removed from the dehydrogenation zone is often first heat exchanged for the dual purposes of lowering its temperature to prevent polymerization of the styrene and for the recovery of heat. The effluent stream may be heat exchanged against a stream of steam, a reactant stream of this or another process or used as a heat source for fractionation. Commercially, the effluent stream is often passed through several heat exchangers for the heating of different streams. The reaction zone effluent may also be passed through a quench zone to rapidly cool it and lessen polymerization. The quench zone may be located after a heat exchange means as shown in U.S. Pat. Nos. 3,515,765 and 3,515,766, or the effluent stream may pass directly from the reactor into the quench zone as shown in U.S. Pat. No. 3,515,764. The cooling media fed to the quench zone is preferably liquid water removed from the phase separation zone. The use of such quench zones is not preferred.

We claim as our invention:
1. A process for dehydrogenating ethylbenzene to styrene which comprises the steps of:
(a) admixing a hereinafter specified vapor stream which comprises steam, ethylbenzene, styrene, and benzene into a feed stream comprising ethylbenzene;
(b) passing said feed stream after said admixture with said stream comprising steam, ethylbenzene, styrene, and benzene as a vapor into a catalytic dehydrogenation zone maintained at dehydrogenation conditions;

(c) withdrawing from said catalytic dehydrogenation zone a vaporous effluent stream comprising ethylbenzene, benzene, styrene and steam;

(d) cooling said vaporous effluent stream withdrawn from said catalytic dehydrogenation zone by indirect heat exchange against said feed stream after said admixture with said stream comprising steam, ethylbenzene, styrene, and benzene;

(e) further cooling said vaporous effluent stream and simultaneously reboiling a water stripping column by generating steam by the indirect heat exchange of said vaporous effluent stream against water removed from the bottom of said water stripping column;

(f) further cooling said vaporous effluent stream and partially condensing said vaporous effluent stream, and passing the partially condensed vaporous effluent stream into a phase separation zone operated at conditions effective to produce a liquid hydrocarbon fraction comprising styrene, benzene, toluene and ethylbenzene and a liquid aqueous fraction containing dissolved ethylbenzene;

(g) withdrawing said liquid hydrocarbon fraction from said phase separation zone as a hydrocarbon stream, and recovering said styrene from said ethylbenzene, benzene and toluene;

(h) withdrawing said liquid aqueous fraction from said phase separation zone as a water stream;

(i) feeding at least a first portion of said water stream into an upper portion of said water stripping column of step (e) under conditions effective to form a stripping column overhead vapor stream comprising steam and ethylbenzene dissolved in said first portion of said liquid water stream, said conditions including a pressure greater than that maintained in said dehydrogenation zone but sufficiently low to allow said water stripping column to be reboiled by indirect heat exchange against said vaporous effluent stream after said effluent stream has been cooled by heat exchange against said feed stream after said admixture with said stream comprising steam, ethylbenzene, styrene, and benzene;

(j) admixing said stripper overhead vapor stream directly into said feed stream as said aforementioned vapor stream of step (a) without intermediate cooling or compression thereof; and, (k) withdrawing a net bottoms stream comprising water which is substantially free of ethylbenzene, benzene and styrene from said water stripping column.

* * * * *